(12) United States Patent
Karlsson

(10) Patent No.: US 7,819,851 B2
(45) Date of Patent: Oct. 26, 2010

(54) ABSORBENT PRODUCT WITH RESEALABLE SIDE PANEL AND METHOD OF MAKING SAME

(75) Inventor: Birgitta Karlsson, Molnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 11/515,249

(22) Filed: Sep. 5, 2006

(65) Prior Publication Data

US 2007/0000987 A1  Jan. 4, 2007

Related U.S. Application Data

(63) Continuation of application No. PCT/SE2004/000341, filed on Mar. 10, 2004.

(51) Int. Cl.
*A61F 13/56* (2006.01)
*A61F 13/62* (2006.01)

(52) U.S. Cl. .................. 604/385.11; 604/386; 604/391; 604/392; 604/396

(58) Field of Classification Search ......... 604/389–391, 604/385.03, 386
See application file for complete search history.

(56) References Cited

U.S. PATENT DOCUMENTS

| | | | | |
|---|---|---|---|---|
| 3,598,114 A | * | 8/1971 | Lewis ........................... | 602/19 |
| 4,315,508 A | * | 2/1982 | Bolick ........................ | 604/371 |
| 4,555,244 A | * | 11/1985 | Buell ......................... | 604/392 |
| 4,753,650 A | * | 6/1988 | Williams .................... | 604/389 |
| 4,850,992 A | * | 7/1989 | Amaral et al. .............. | 604/389 |
| 4,988,346 A | * | 1/1991 | Pfefferkorn ................. | 604/389 |
| 5,108,385 A | * | 4/1992 | Snyder ....................... | 604/397 |
| 5,170,505 A | * | 12/1992 | Rohrer ........................... | 2/69 |
| 5,370,634 A | * | 12/1994 | Ando et al. ............. | 604/385.21 |
| 5,401,275 A | * | 3/1995 | Flug et al. ................... | 604/391 |
| 5,531,732 A | * | 7/1996 | Wood .......................... | 604/391 |
| H1674 H | * | 8/1997 | Ames et al. ................. | 604/389 |

(Continued)

FOREIGN PATENT DOCUMENTS

CN  1212615  3/1999

(Continued)

OTHER PUBLICATIONS

International Search Report from PCT/SE2004/000341.

(Continued)

*Primary Examiner*—Karin M Reichle
(74) *Attorney, Agent, or Firm*—Buchanan Ingersoll & Rooney PC

(57) ABSTRACT

An absorbent product (32) and a method of making the absorbent product. The absorbent product has at least one side panel (2, 35) having a first panel section (9) configured with a first tab (16) and a second panel section (10) configured with a second tab (23), wherein the first tab (16) overlaps and is fastened by a fastener (6), such that it can be opened and resealed, to an outer side (30) present on the second panel section (10), wherein the second tab (23) overlaps and is fastened by a fastener, such that it can be opened and resealed, to an outer side (31) present on the first panel section (9), and wherein the outer side (31) of the first panel section (9) faces the same way as the outer side (30) of the second panel section (10).

10 Claims, 6 Drawing Sheets

U.S. PATENT DOCUMENTS

| | | | |
|---|---|---|---|
| 5,851,205 A | 12/1998 | Hisada et al. | |
| 5,873,870 A * | 2/1999 | Seitz et al. | 604/385.04 |
| 5,876,531 A | 3/1999 | Jacobs et al. | |
| 6,123,694 A * | 9/2000 | Pieniak et al. | 604/385.28 |
| 6,432,098 B1 * | 8/2002 | Kline et al. | 604/387 |
| 6,579,275 B1 | 6/2003 | Pozniak et al. | |
| 6,596,107 B2 | 7/2003 | Stopher | |
| 6,648,866 B2 * | 11/2003 | Magee et al. | 604/385.03 |
| 6,652,497 B1 * | 11/2003 | Suprise | 604/385.01 |
| 6,911,023 B1 * | 6/2005 | Hamilton et al. | 604/387 |
| 7,252,658 B2 * | 8/2007 | Sayama | 604/396 |
| 2003/0032933 A1 * | 2/2003 | Sayama | 604/386 |
| 2003/0135184 A1 | 7/2003 | Van Gompel et al. | |
| 2003/0212377 A1 | 11/2003 | Karlsson et al. | |

FOREIGN PATENT DOCUMENTS

| | | |
|---|---|---|
| EP | 0 755 665 A1 | 1/1997 |
| WO | WO 97/32555 | 9/1997 |
| WO | WO 0211657 A2 * | 2/2002 |
| WO | WO 03/057116 | 7/2003 |

OTHER PUBLICATIONS

Written Opinion from PCT/SE2004/000341.

Notification of the First Office Action in CN 200480042354.7 dated Feb. 20, 2009, and an English Translation thereof.

Russian Office Action in corresponding Application No. 2006132338/14(035172) dated Dec. 25, 2007, and an English Translation thereof.

An English Translation of the Colombian Office Action in corresponding Application No. 06090484 dated Jun. 9, 2008.

* cited by examiner

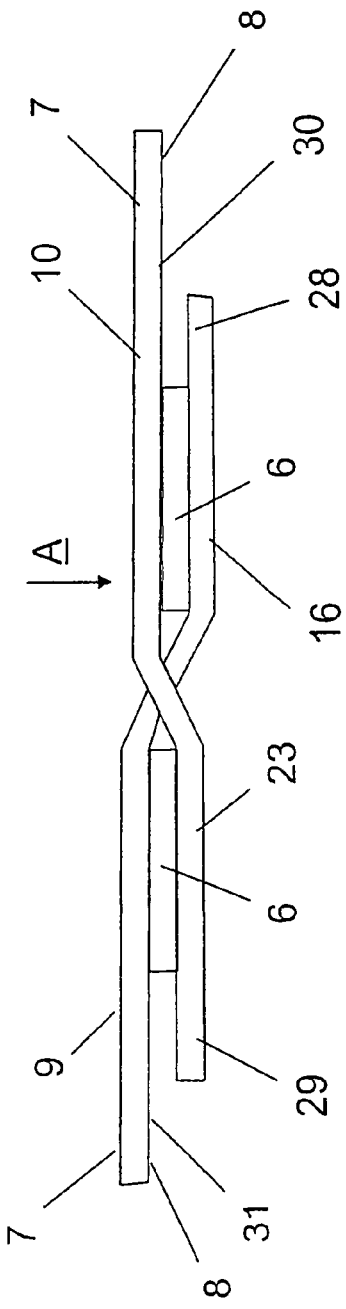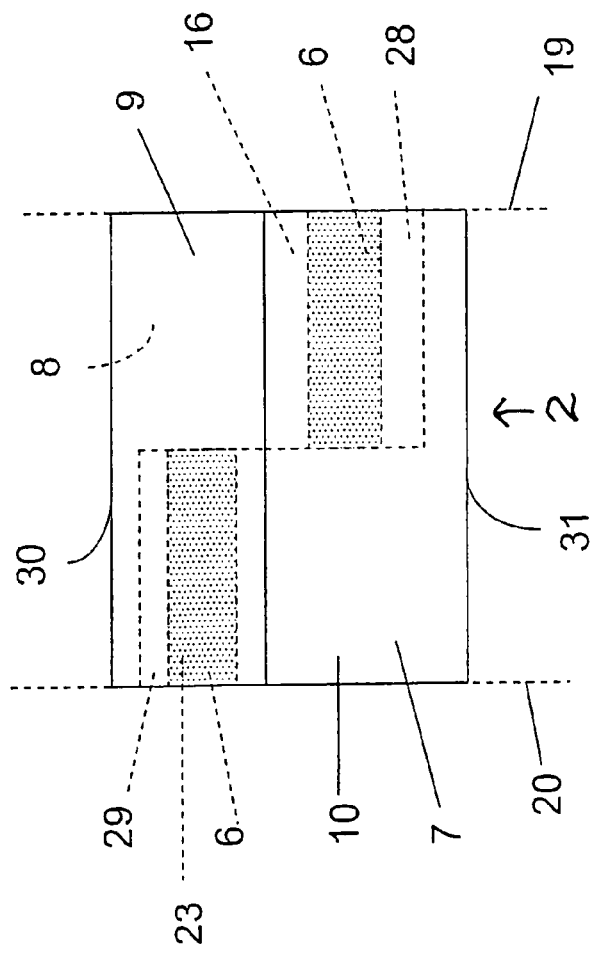

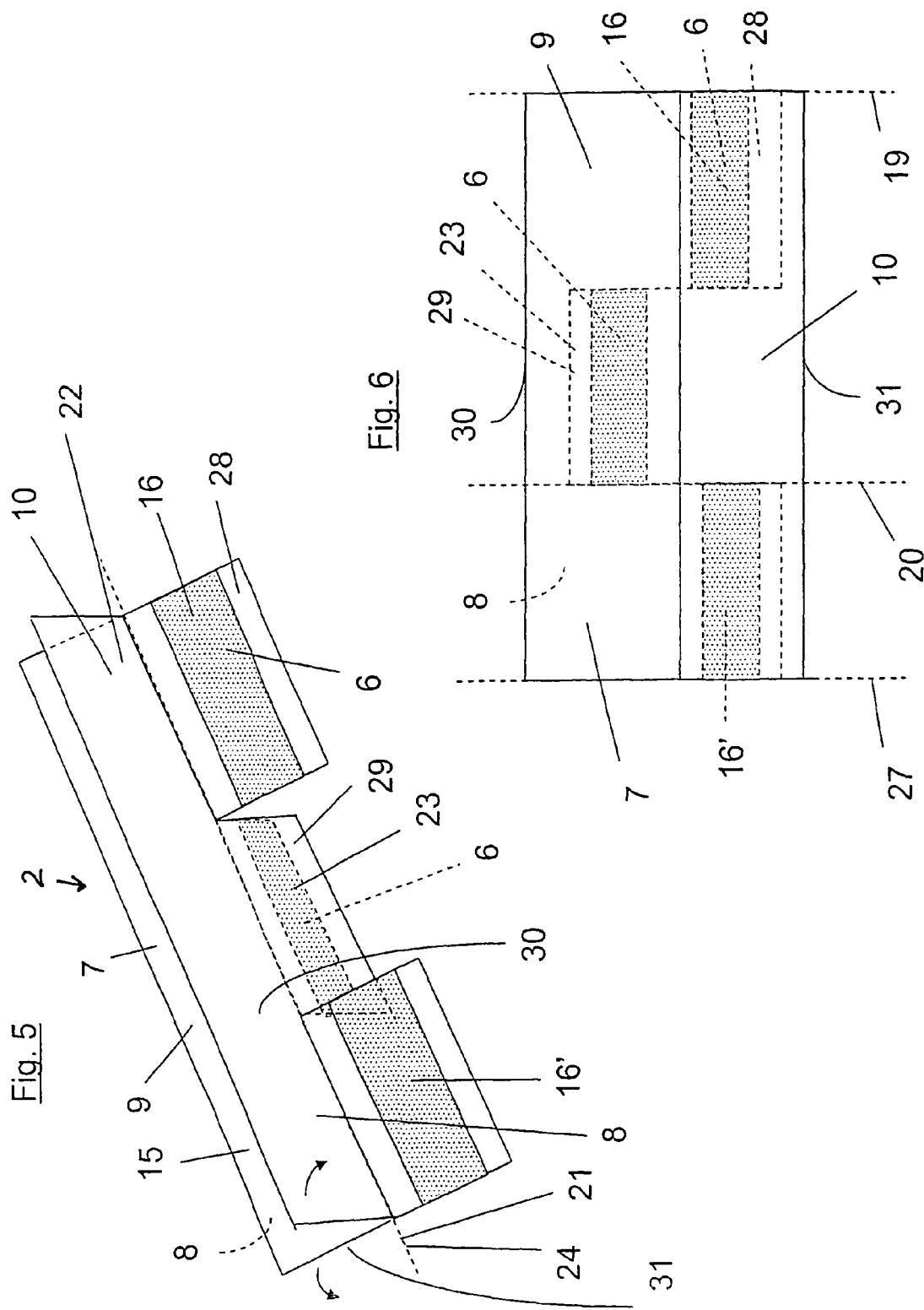

ABSORBENT PRODUCT WITH RESEALABLE SIDE PANEL AND METHOD OF MAKING SAME

CROSS-REFERENCE TO RELATED APPLICATIONS

The present application is a continuation-in-part of PCT/SE2004/000341, filed in Sweden on Mar. 10, 2004 and which designated the United States. The entire contents of PCT/SE2004/000341 is incorporated herein by reference.

TECHNICAL FIELD

The present invention relates to an absorbent product, such as a pull-up diaper, comprising a front panel, a back panel and, therebetween, two opposing side panels, and a crotch section. The invention further relates to a method of making a side panel for a pull-up diaper.

RELATED ART

Pull-up diapers, unlike standard diapers, are configured with whole side panels. Pull-up diapers are preferably slipped over the legs and hips of a user. Pull-up diapers give a good fit and good stability, since they are configured in one whole piece. Pull-up diapers are used by children and also by adults suffering from incontinence.

It is previously known to configure pull-up diapers with side panels comprising a side seam configured to split when subjected to a load over a certain level. Such a load is preferably generated by the carer or the user who wishes to open the side panel by tearing the side panel along the seam. After having opened the pull-up diaper by way of the side seam, the user or the carer can inspect the inside of the pull-up diaper and assess to what extent a change of diaper is necessary or not. In such previously known pull-up diapers, it is further known to equip the pull-up diaper with a resealable fixing device in the form of a tab equipped with fixing means. The fixing device is fixedly anchored on one side of the seam and on the other side of the seam there is an attachment zone intended to receive and attract the fixing means. When the user wishes to reseal the pull-up diaper, the tab is brought over the torn-open seam, whereupon the fixing means is fixed onto the attachment zone. The fixing device can comprise mechanical fastening means, for example VELCRO[®] tape, or fastening means in the form of adhesive.

One problem with the prior art is that the tab/the fixing device has to be secured to the side panel at a specific place, thereby creating a factor which limits the production speed. Moreover, the attachment zone has to be applied to a specific place on the side panel, which also limits the production speed. Another problem is that the side panel comprises a tearable seam, which, firstly, has to be specially configured and, secondly, can be difficult for a user to get open. Moreover, the seam can touch against the skin of the user in such a way that the user experiences discomfort. Further problems are that the tab can be easily opened by a child.

There is therefore a requirement for an improved pull-up diaper in which the above problems are reduced or eliminated.

OBJECTS AND SUMMARY

The present invention aims to solve the problems described above a pull-up diaper with improved functioning and a method of making such a pull-up diaper.

The present invention relates to an absorbent product, such as a pull-up diaper, comprising a front panel, a back panel and, therebetween, two opposing side panels and a crotch section. The pull-up diaper further advantageously comprises an absorption body extending from the front panel to the back panel via the crotch section.

In one embodiment, at least one of the side panels comprises a first panel section configured with a first tab and a second panel section configured with a second tab. The first tab overlaps and is fastened by a fastener, such that it can be opened and resealed, to an outer side of the second panel section, and the second tab overlaps and is fastened by a fastener, such that it can be opened and resealed, to an outer side of the first panel section. The outer side of the first panel section faces essentially the same way as the outer side of the second panel section. The first tab and the second tab are therefore located on the same side of the side panel. Both the first and the second panel section can be configured to form whole side panels, but can also be configured to constitute just a part-quantity of the respective side panel.

One advantage with the embodiment is that the side panel, because of the positioning of the panel sections, remains flexible, even though the fastening means may be constituted by intrinsically hard/stiff materials. The tabs constitute flexible parts of the side panel, which makes the side panel more pliable.

Another advantage is that shearing forces generated in the panel whilst the diaper is in use are absorbed better than in products comprising whole side panels. The tabs constitute parts of the side panel which distribute the shearing forces more advantageously than does a whole side panel. A whole side panel is at risk of crumpling up, instead of, like the tabs, absorbing shearing force of varying magnitude.

A further advantage is that the tabs are fitted on the same side of the side panel, e.g., on the outer side or the inner side of the side panel, which affords a user easy access to all the tabs. The tabs are opened by every alternate tab being pulled in one direction and every other alternate tab in the opposite direction. This is advantageous, since an adult user or carer can easily open the side panel by pulling the tabs in the opposite direction. On the other hand, such a manoeuvre is hard for a child, who therefore has difficulties in opening the side panel by his or her self. If the side panel had instead been assembled with only one tab, the child would easily have been able to open the diaper by guiding the tab in one direction, which possibility is undesirable.

Another advantage is that the tabs can produce an open structure in the side panel, which thereby becomes more breathable than a whole side panel.

The side panel may be produced by a method in which the side panel is made from a material web having a middle segment which, in a latitudinal direction, is limited by first and second side segments located on either side, which side segments, like the middle segment, run in a production direction. The method comprises the steps of:

the middle segment of the material web being lined in the production direction with a fastener material, which is fixed onto it;

dividing the lined material web into a first panel section and a second panel section by, in the production direction, slitting the material web, in a continuous curved pattern undulating about a center line present on the material web, in such a way that the middle segment is cut with each traversing stroke, in the first panel section a first tab being formed in the direction away from the first side segment toward the second side segment, and in the second panel section a second tab being formed in the direction away from the second side segment toward the first side segment;

the side panel being formed by:

the first panel section being brought toward the second panel section in such a way that the first tab overlaps an outer side present on the second panel section and wherein the second tab overlaps an outer side present on the first panel section, wherein the two outer sides face essentially the same way;

the first tab being fastened, such that it can be opened and resealed, to the outer side of the second panel section;

the second tab being fastened, such that it can be opened and resealed, to the outer side of the first panel section;

the material web, before or after the first panel section having been brought toward the second panel section, being divided essentially perpendicularly to the production direction along a first line and a second line essentially parallel with the first line, wherein the first tab and the second tab are located between the first line and the second line.

In those cases where the material web is divided before the first panel section has been brought toward the second panel section, the side panel is made in batches, i.e., panel by panel.

In those cases where the material web is divided after the first panel section has been brought toward the second panel section, the side panel is made in a continuous process. The continuous process comprises a point after which the side segments have been brought toward each other in such a way that all the tabs are located on the same side of the web and wherein the size of the panels can be chosen by laterally dividing the brought-together web at a suitable place.

One advantage of the method is that the advantageous panel described above is made without any material wastage. Another advantage is that the size of the side panel can easily be determined by the width of the material web.

In one embodiment of the invention, the slitting is realized in a continuous pattern in which a first cut is made essentially in the production direction, followed by a second cut across the middle segment essentially perpendicular to the production direction, followed by a third cut essentially in the production direction, followed by a fourth cut across the middle segment. The fourth cut, the first cut and the second cut form the first tab of the first panel section. The second cut, the third cut and another fourth cut form the second tab of the second panel section.

The first cut is advantageously made in the second side segment at a distance from the middle segment. The distance between the middle segment and the first cut creates a part of the first tab which is free from fastening means and which, therefore, advantageously constitutes a first gripping part. The third cut is advantageously made in the first side segment at a distance from the middle segment. The distance between the middle segment and the third cut creates a part of the second tab which is free from fastening means and which, therefore, advantageously constitutes a second gripping part. The gripping parts can advantageously be used by a user in detaching the tabs.

In one embodiment of the invention, the first line coincides with a fourth cut and the second line coincides with another fourth cut. The first line is at least at such a distance from the first line that the first tab and the second tab are located between the lines. Depending on where on the material web the first line and the second line are placed, more than two tabs may be obtained between the lines, i.e. in the side panel. It is possible, for example, for the second line to coincide with the second cut, at such a distance from the first line that two first tabs, and a second tab situated therebetween, are located between the lines.

According to one embodiment, the tabs are equal in size. Both the first tab and the second tab are advantageously rectangular, but can be constituted by a different suitable geometry which allows the panel sections to be able to be pushed together in such a way that all the tabs end up on the same side of the side panel.

According to one embodiment of the invention, the fastening means comprise a mechanical fastening means. The mechanical fastening means are preferably constituted by elements (male members) of the kind which mechanically fix in the material forming the side panel. Suitable such elements are, for example, hook-shaped, knob-shaped, arrow-head-shaped, or otherwise suitably configured male members, which can fix in the structure of the side panel. It is known to use so-called VELCRO[®] material with male members which can comprise any of the abovementioned element types and are arranged to fix in a receiver material. The receiver material is preferably constituted by female members, i.e. a material having a structure which allows the male members to fix in the female members. The female members can be constituted by, for example, eyelets or similar loop-like devices. The receiver material can also in certain cases be constituted by male members, i.e. a male member in the fastening means fixes in another male member in the receiver material.

The material web is lined with the fastening means in such a way that it, in the side panel, covers parts of or the whole of the tabs. The fastening material is intended to fix in the material structure constituting the material web, i.e. the material web shall comprise a structure comprising female members in which the male members can fix. Such female members can be constituted, for example, by eyelets or similar open or half-open structures. The fastening means of the tabs are therefore advantageously fixed by male members in female members present in the respective panel section. Suitable such materials are, for example, non-woven fibre materials, i.e. a so-called nonwoven, or woven materials, or other materials suitable for the purpose.

In order to prevent the fastening means from catching in the side panel material when the panel sections are brought toward each other, the fastening means can be lined with a material layer which fixes to the fastening means but which prevents the fastening means from catching in the panel section. Once the tabs are in the right place, the material layer is removed and the tabs can be fixed onto the respective outer sides of the panel sections. The material layer can consist of a strip placed on the fastening means before the fastening means is applied in the middle segment, or else the material layer can be placed on the fastening means after the fastening means has been fixed onto the middle section.

The fastening means can be fixed to the material web in the middle segment by an adhesive or some other suitable fastening means.

In one embodiment of the invention, the side panels are constituted by a non-elastic material. The side panels can, however, consist of an elastic material. The side panel is advantageously made of a non-woven fibre material, a so-called nonwoven, but can also be made of some other suitable material having a structure which allows the fastening means to fix in the side panel material.

In one pull-up diaper, the side panel can be supplemented by a seam connecting the first panel section to the second panel section. The seam is advantageously of such a kind that it can be broken by a user, as the need arises. One example of such an occasion is where the absorbent product has been used for a while and a user, carer or parent wishes to check the content of the product. In this instance, the seam is broken and the side panel is opened, whereafter a simple visual inspection of the content becomes possible. If it is thought in the visual inspection that continued usage is possible, then the tabs are used as resealable means in the side panel. The seam can be formed by any type of suitable method, for example gluing, or welding.

The invention also relates to an absorbent product, such as a pull-up diaper, comprising a side panel which can be made by a method according to the above.

DESCRIPTION OF THE FIGURES

The invention will be described below in connection with a number of figures, in which:

FIG. 3 shows a side view of a side panel according to FIG. 2;

FIG. 4 shows a top view of a side panel according to FIG. 2 and FIG. 3 in the direction of the arrow A in FIG. 3;

FIG. 5 shows an embodiment of the invention in which the material web has been divided along the first and third line shown in FIG. 4;

FIG. 6 shows a top view of a side panel according to FIG. 5;

FIG. 7 shows a pull-up diaper according to an embodiment of the invention, and in which

PREFERRED EMBODIMENTS

Figure 1:
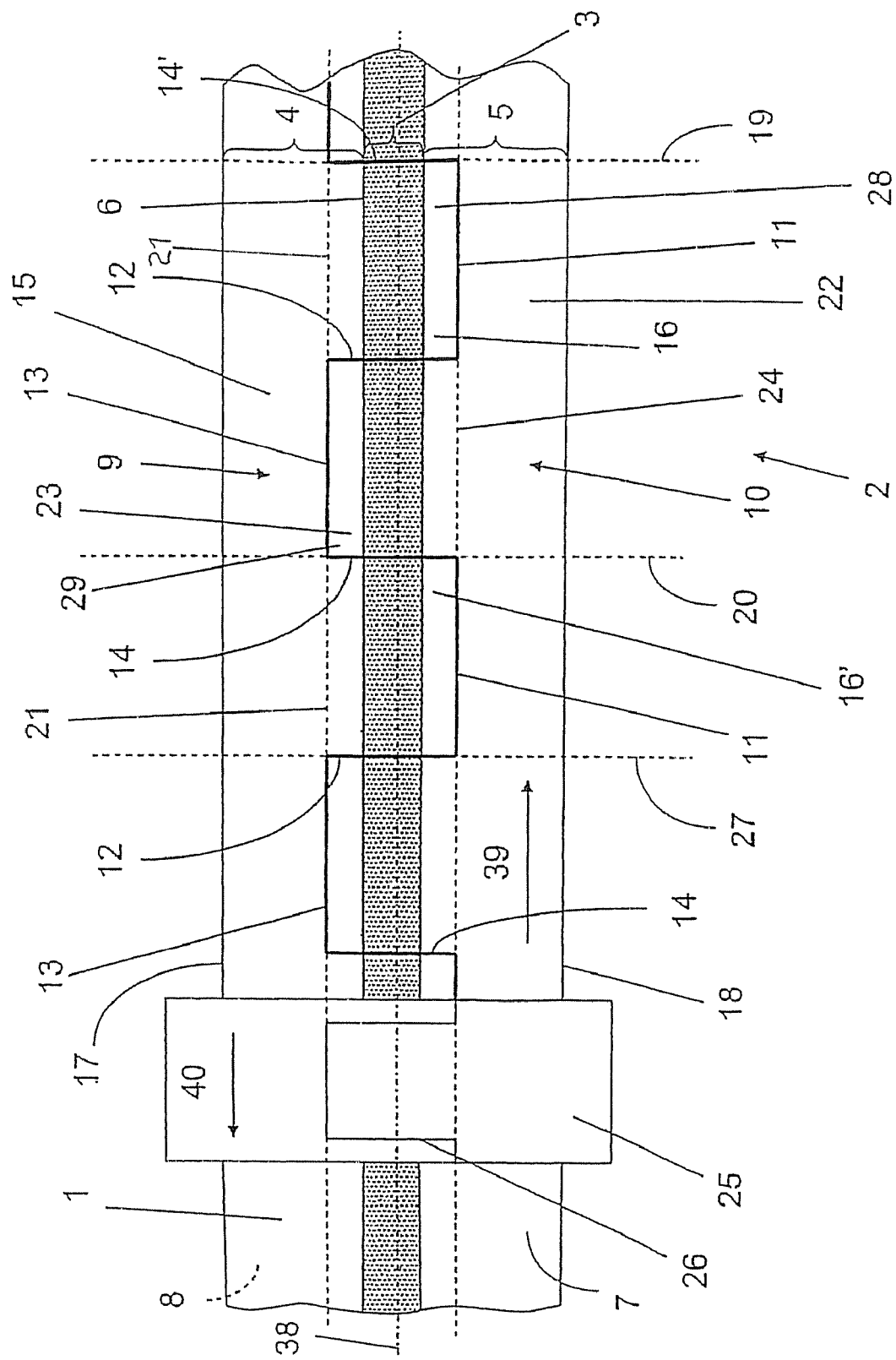
FIG. 1 shows a material web for making a side panel according to an embodiment of the invention.

FIG. 1 shows a material web 1 for making a side panel 2 according to an embodiment of the invention. The material web 1 runs in a production direction, which, in FIG. 1, is marked by an arrow 39 pointing in the production direction. The material web 1 has a middle segment 3, which, in the latitudinal direction (lateral direction in relation to the production direction), is limited by a first and a second side segment 4, 5, which side segments, like the middle segment 3, have an extent in the production direction. FIG. 1 depicts that the middle segment 3 of the material web has been lined in the production direction with a fastener or fastening means 6. The material web 1 has an upper side 7 and a lower side 8 and is limited in the lateral direction by a first edge 17 and a second edge 18. FIG. 1 depicts that the fastening means 6 is affixed to the upper side 7.

FIG. 1 further shows that the lined material web is divided into a first panel section 9 and a second panel section 10. The division is made by making cuts, in the production direction, in a continuous curved pattern undulating about a center line 38. FIG. 1 depicts a first cut 11 made essentially in the production direction, followed by a second cut 12 made across the middle segment 3 essentially perpendicular to the production direction, followed by a third cut 13 made essentially in the production direction, followed by a fourth cut 14 made across the middle segment 3. The four cuts 11-14 are repeated continually along the whole of the material web 1 as the material web 1 is advanced in the production direction.

FIG. 1 shows a first line 19 extending in the lateral direction and coinciding with the fourth cut 14'. FIG. 1 further shows a second line 20 extending in the lateral direction and coinciding with another fourth cut 14, at a distance from the first line 19. The first line 19 and the second line 20 constitute two suitable lines along which the material web can be cut in the lateral direction so as thereby to obtain the basic frame for the side panel 2. After the material web 1 has been cut along the first line 19 and the second line 20, the side panel 2 comprises the first panel section 9 and the second panel section 10.

The first panel section 9 comprises a first side portion 15 and a first tab 16. The first side portion 15 is limited by the first edge 17, the first line 19, the second line 20 and a third line 21 coinciding with the third cut 13. The first tab 16 also has a rectangular configuration, but is smaller than the first side portion 15 and has an extent in the production direction essentially between the fourth cut 14' and the second cut 12. The first tab 16 is limited in its lateral extent by the third line 21 and the first cut 11.

The second panel section 10 comprises a second side portion 22 and a second tab 23. The second side portion 22 is limited by the second edge 18, the first line 19, the second line 20 and a fourth line 24 coinciding with the first cut 11. The second tab 23 also has a rectangular configuration, but is smaller than the second side portion 22 and has an extent in the production direction essentially between the second cut 12 and the fourth cut 14. The second tab 23 is limited in its lateral extent by the fourth line 24 and the third cut 13.

FIG. 1 shows a roller 25 provided with cutting tools 26, which are pressed against the material web 1 in such a way that the cutting tools 26 continuously cut the material web 1 according to the curved pattern as the material web 1 is fed in the production direction. The roller 25 rotates in the direction shown by the arrow 40. The cuts 11-14 do not need to be realized with a roller 25, but can be realized using any suitable method whatsoever, for example punching, shearing or water-based cutting method (so-called water jetting).

FIG. 1 shows that the fourth cut 14', the first cut 11 and the second cut 12 form the first tab 16 of the first panel section 9 and that the second cut 12, the third cut 13 and the fourth cut 14 form the second tab of the second panel section 10. The first tab 16 extends from the first side segment 4 in the direction of the second side segment 5. The second tab 23 extends from the second side segment 5 in the direction of the first side segment 4.

FIG. 1 shows a fifth line 27, parallel with the first and the second line 19, 20, running essentially perpendicular to the production direction. The parallel lines 19, 20, 27 mark places that divide the material web in order to obtain, for example, a desired size of side panel 2 or a desired number of tabs 16, 23. If the material web is divided along the first line 19 and the second line 20, the side panel acquires two tabs, namely the first tab 16 and the second tab 23. If, on the other hand, the material web is divided along the first line 19 and the fifth line 27, the side panel 2 acquires three tabs, namely two first tabs 16, 16' and a second tab 23 situated therebetween. Similarly, by dividing the material web 1 at appropriate places, more than three tabs may be chosen. The size of the side panel 2 does not, however, need to increase with the number of tabs 16, 23; instead, the tabs 16, 23 can be made narrower, giving an increased number of tabs 16, 23 per given length of the material web 1 in the production direction. If the tabs 16, 23 are made narrower, a side panel 2 with a greater number of tabs 16, 23 is therefore obtained, even though the size of the side panel 2 is maintained. The size of the tabs 16, 23 is varied with the configuration of the curved pattern. The shorter are made the first and third cut 11, 13 and the narrower become the tabs 16, 23, the greater the number of tabs 16, 23 which are accommodated within the framework of two lines at constant distance apart.

FIG. 1 depicts that the first cut 11 is situated in the second side segment 5 and that the third cut 13 is situated in the opposing first side segment 4. This results in the fastening means 6 only covering parts of the tabs 16, 23, which has the advantage that a part of the tab 16, 23 can constitute a gripping part 28, 29. In FIG. 1 it can be seen that the first tab 16 extends from the first side segment 4 across the middle segment 3 and into the second side segment 5. The first gripping part 28 here consists of parts of the second side segment 5. Similarly, the second tab 23 extends from the second side segment 5 across the middle segment 3 and into the first side segment 4. The second gripping part 29 here consists of parts of the first side segment 4. The first cut 11 and the third cut 13 do not need to be placed in the side segments 4, 5, but can instead be placed in the boundary cut between the side segments 4, 5 and the middle segment 3. The tabs 16, 23 are in this case fully lined with the fastening means 6.

Figure 2:
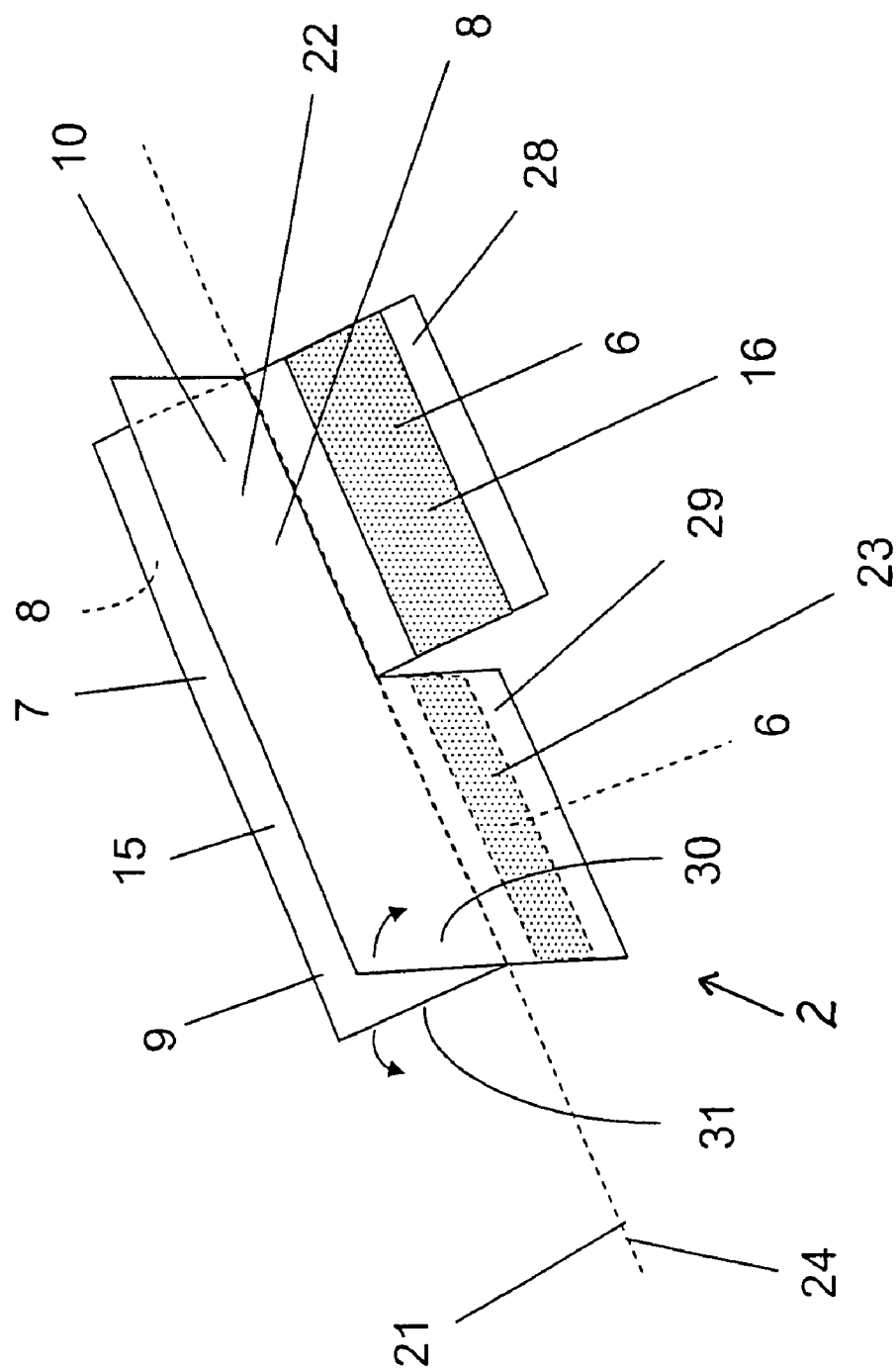
FIG. 2 shows an embodiment of the invention in which the material web has been divided along the first and second lines shown in FIG. 1.

In FIG. 2 a first embodiment of the invention is shown, in which the material web 2 has been divided along the first and second line 19, 20 shown in FIG. 1. The first tab 16 and the second tab 23 are located between the first line 19 and the second line 20.

FIG. 2 shows that the side panel 2 is formed by both the first panel section 9 and the second panel section 10 having been folded down in relation to the plane in which the material web 1 lay. To put it another way, the first panel section 9 has been rotated about an axis constituting the third line 21 and the second panel section 10 has been rotated in the opposite direction about an axis constituting the fourth line 24. As a result of the folding-down/rotation, all the tabs 16, 23 are facing essentially the same way. The folding-down/rotation does not need to be done to any particular angle, but rather the purpose of the folding-down is to prevent the tabs 16, 23 from lying in the same plane. The tabs 16, 23 should be at an angle to each other. An alternative to folding/rotating the whole of the first and the whole of the second panel section 9, 10 is to fold down just the tabs 16, 23. The tabs 16, 23 do not, of course, necessarily have to be folded down, but can also be folded up if the lower side 8 of the material web 2 has been lined with the fastening material 6 instead of, as in FIG. 1, the upper side 7. This is, however, merely a question of reference point for an observer.

FIG. 2 further shows that the first panel section 9 has been brought toward the second panel section 10 in such a way that the first tab 16 overlaps an outer side 30 present on the second side portion 22 and that the second tab 23 overlaps an outer side 31 present on the first side portion 15. FIG. 2 depicts that the two outer sides 30, 31 face the same way. The two outer sides 30, 31 coincide in the material web 2 with the lower side 8 of the material web.

FIG. 2 depicts that the first panel section 9 and the second panel section 10 have been brought together in such a way that the edge belonging to the first cut 11 in the second side portion 22 is aligned with the edge belonging to the third cut 13 in the first side portion 15. To put it another way, with reference to FIG. 1, the first panel section 9 has been brought toward the second panel section 10 in such a way that the third line 21 and the fourth line 24 coincide.

FIG. 3 shows a side view of a side panel according to FIG. 2, in which the first tab 16 has been fastened by the fastening means 6 to the outer side 30 of the second panel section 10 and the second tab 23 has been fastened by the fastening means 6 to the outer side 31 of the first panel section 9. The fastening means 6 can be opened and resealed and consist, preferably, of mechanical fastening means.

FIG. 3 depicts that the fastening means 6 only constitute a part of the tabs 16, 23. One advantage with this is that the outer part of each tab 16, 23 can constitute the gripping part 28, 29 described above, which gripping part can help a user having to undo the tabs 16, 23.

FIG. 4 shows a top view of a side panel according to FIG. 2 and FIG. 3, in which it is evident that the two tabs 16, 23 fix together the side panel 2 by means of the fastening means 6. The top view is shown in the direction of the arrow A in FIG. 3. FIG. 4 shows the tabs 16, 23 placed on the bottom side of the side panel observed from the top view in question. The tabs 16, 23 are therefore marked with dashed lines.

In FIG. 5 a second embodiment of the invention is shown, in which the material web 1 has been divided along the first and fifth line 19, 27 shown in FIG. 1. The first tab 16 and the second tab 23 are located between the first line 19 and the fifth line 27, together with a further first tab 16'.

FIG. 5 shows that the side panel 2 is formed by both the first panel section 9 and the second panel section 10 having been folded down in relation to a common plane. As in the embodiment described in connection with FIG. 3, this can otherwise be described in terms of the first panel section 9 having been rotated about an axis constituting the third line 21 and the second panel section 10 having been rotated in the opposite direction about an axis constituting the fourth line 24. As a result of the folding-down, all the tabs 16, 16', 23 are facing essentially the same way. The folding-down/rotation does not need to be done to any particular angle, but rather the purpose of the folding-down is for the tabs 16, 16', 23 not to lie in the same plane but rather be at an angle to each other. An alternative to folding the first and the second panel section 9, 10 is to fold down just the tabs 16, 16' 23. The tabs 16, 16', 23 do not, of course, necessarily have to be folded down, but can also be folded up when the fastening means 6 is disposed on the lower side 8 of the material web 2. This is merely a question of reference point for an observer.

FIG. 5 further shows that the first panel section 9 has been brought toward the second panel section 10 in such a way that the first tab 16 overlaps the first outer side 30 present on the second side portion 22 and that the second tab 23 overlaps the second outer side 31 present on the first side portion 15. FIG. 5 depicts that the two outer sides 30, 31 face the same way. The two outer sides 30, 31 coincide in the material web 2 with the lower side 8 of the material web.

FIG. 5 depicts that the first panel section 9 and the second panel section 10 have been brought together in such a way that the edge belonging to the first cut 11 in the second side portion 22 is aligned with the edge belonging to the third cut 13 in the first side portion 15. To put it another way, with reference to FIG. 1, the first panel section 9 has been brought toward the second panel section 10 in such a way that the third line 21 and the fourth line 24 coincide.

FIG. 6 shows a top view of a side panel according to FIG. 5, in which it is evident that three tabs 16, 16', 23 fix together the side panel 2. FIG. 6 shows the tabs 16, 16', 23 placed on the bottom side of the side panel observed from the top view in question. The tabs 16, 16', 23 are therefore marked with dashed lines.

Figure 7:
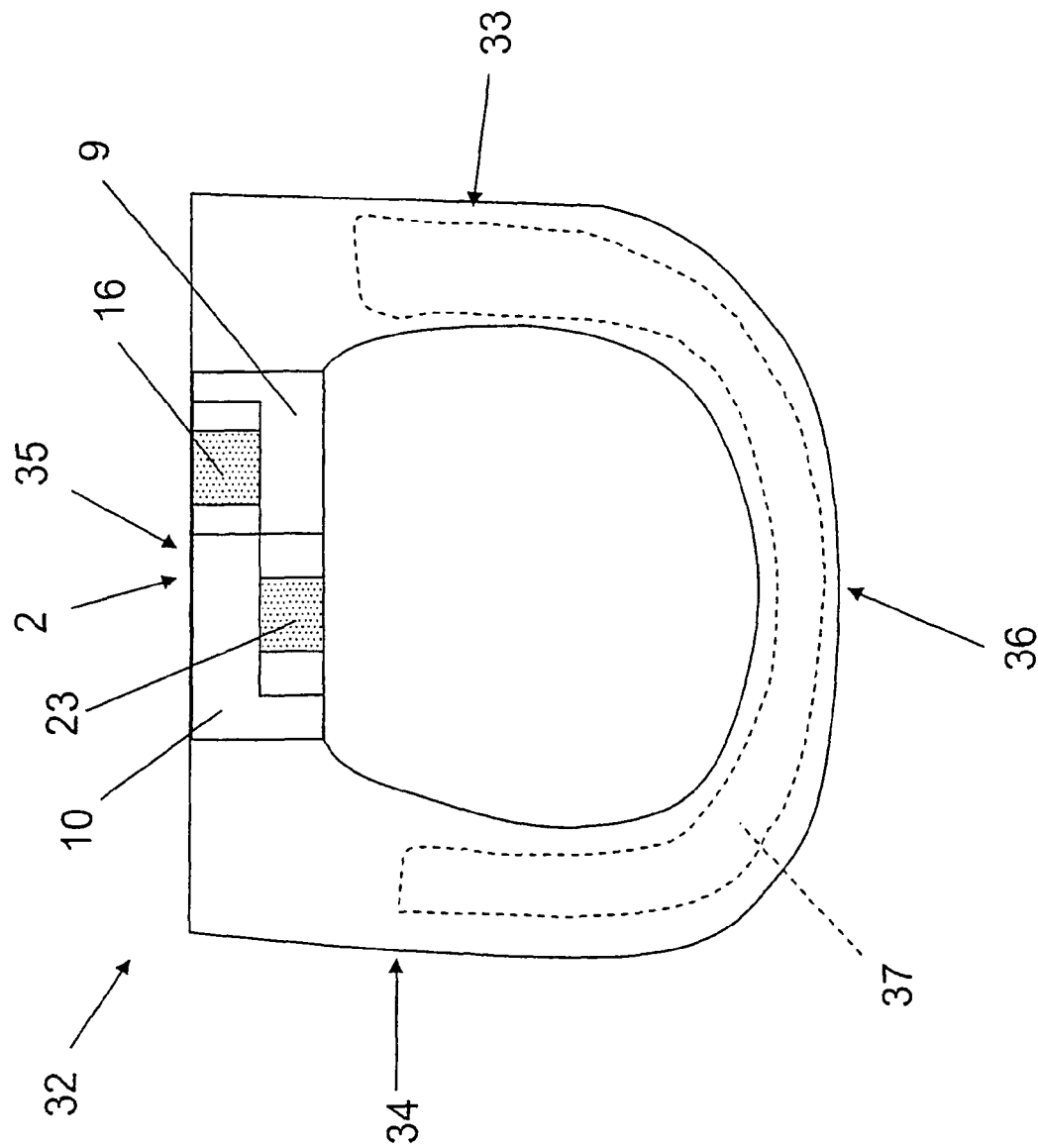

FIG. 7 shows a pull-up diaper 32 according to an embodiment of the invention, comprising a front panel 33, a back panel 34 and, therebetween, two opposing side panels 35, and a crotch section 36. The pull-up diaper also comprises an absorption body 37 intended to receive and wholly or partially absorb urine, menstrual fluids and excrement from a user. FIG. 7 depicts that at least one side panel 35 is constituted by a side panel 2 according to the invention described in connection with FIGS. 2-4. FIG. 7 shows the tabs 16, 23 placed on the outer side of the side panel 2, i.e., on that side of the side panel 2 which faces away from a user when the pull-up diaper 32 is in use. In another embodiment of the invention, the tabs 16, 23 can be placed on the inner side of the pull-up diaper 33. FIG. 7 depicts that the side panel 2 corresponds to the side panel 35, but the side panel 2 can constitute a part-quantity of the side panel 35.

Figure 8:
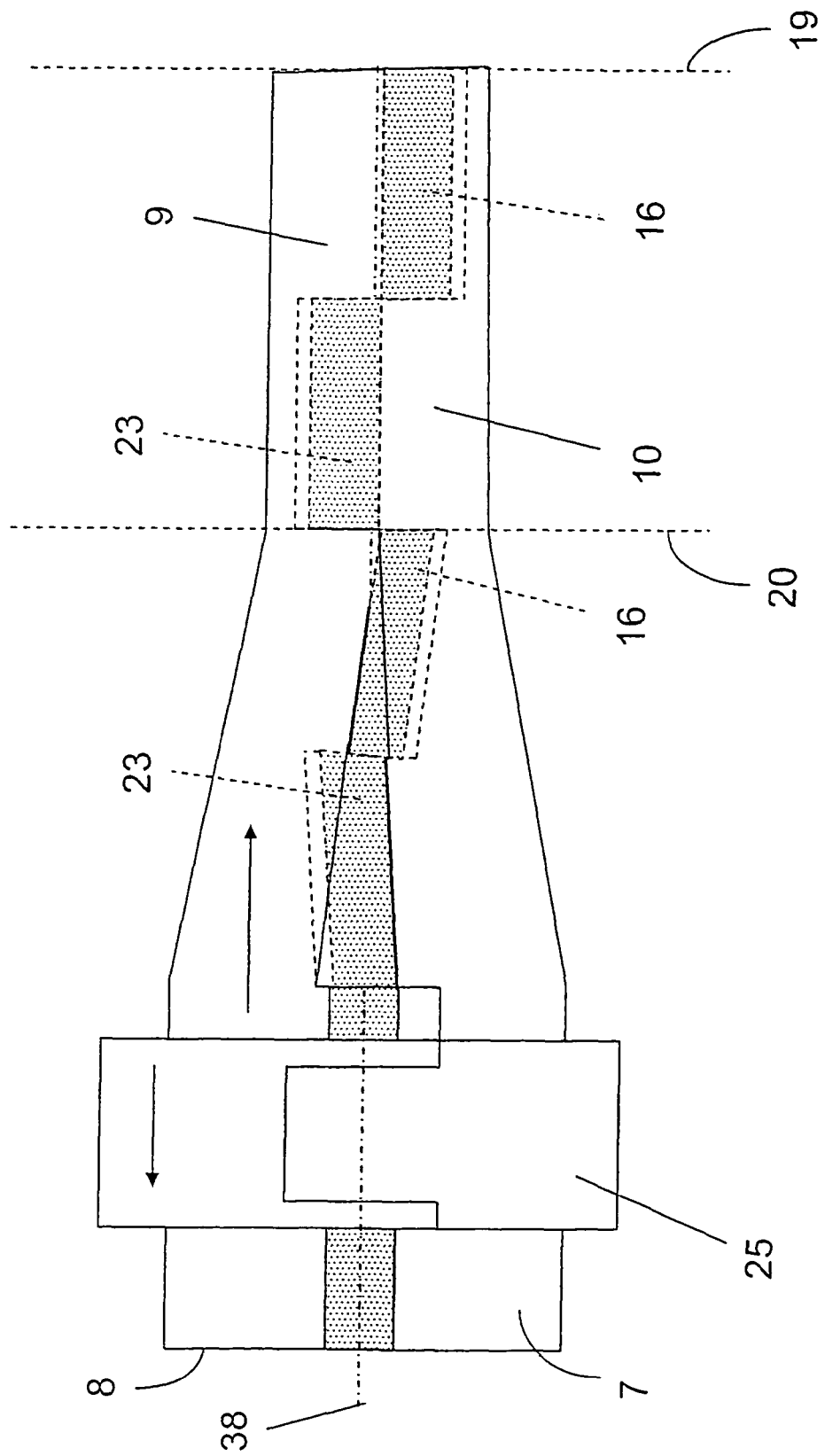
FIG. 8 shows a continuous process for making a side panel according to an embodiment of the invention.

FIG. 8 shows an embodiment of the invention in which the first panel section 9 is brought toward the second panel section 10 in a continuous process. After the panel sections 9, 10 have been brought together, the tabs 16, 23 are fixed to the respective outer side 30, 31 according to the description of the embodiments in connection with FIGS. 1-7.

In the said embodiment, a removable layer (not shown) is disposed on the fastening means 6. The removal layer is constituted, preferably, by a material which does not attach to the material constituting the side panel. The removable layer allows the two panel sections 9, 10 to be pushed toward each other without the fastening means inadvertently taking hold before the tabs 16, 23 are in correct position. Once the tabs 16, 23 are in correct position, the removable layer is taken off, whereupon the fastening means fixes the tabs 16, 23 to the outer sides 30, 31 of the side portions 15, 22. After the tabs 16, 23 have been fixed together, the brought-together material web can be cut at appropriate places in order to obtain a side panel according to the invention described in any of the embodiments according to FIGS. 1-7.

The invention is not limited to the above-stated embodiments, but can be varied within the scope of the following patent claims and equivalents thereof. As an example, the tabs can be elastic and equipped with markings indicating how far the tabs have stretched. Such stretching, combined with knowledge of the material in the tab, provides information on the load to which the diaper is subjected, i.e., the pressure exerted by the diaper upon a user.

Another example is that the curved pattern in FIG. 1, which is dentate, can be realized in other patterns. As an example, the second and the fourth cuts 12, 14 can be made angled in such a way that the tabs acquire the shape of a parallel trapezium. The second and fourth cuts 12, 14 do not need to be straight but can actually be curved, for example, parts of a sine shape. The first and the third cuts 11, 13 should preferably be straight cuts essentially parallel with the production direction.

What is claimed is:

1. An absorbent product, comprising a front panel, a back panel, two opposing side panels arranged between the front panel and the back panel, and a crotch section arranged between the front panel and the back panel; at least one of the side panels having opposed lateral edges non-releasably connected to the front panel and back panel, respectively, the at least one of the side panels further comprises a first panel section and a second panel section adjacent the opposite lateral edges, respectively, and the first panel section connected to the second panel section by a seam adapted to be non-resealably broken by a user to open the side panel, said first panel section configured with a first side portion and a first tab and a second panel section configured with a second side portion and a second tab, wherein the first tab includes a fastened side and an opposite unfastened side and overlaps the second panel section and is fastened by a fastener on the fastened side such that it can be opened and resealed, directly to an outer surface side of the second side portion, wherein the second tab includes a fastened side and an opposite unfastened side and overlaps the first panel section and is fastened by a fastener on the fastened side, such that it can be opened and resealed, directly to an outer surface side of the first side portion, wherein, in a fastened state, the first tab and the second tab do not overlap each other in plan view, and the outer surface side of the first panel section faces essentially the same way as the outer surface side of the second panel section, the entire unfastened sides of the first tab and the second tab face essentially the same way as the outer surface sides of the first and second panel sections and define an outermost surface of the at least one of the side panels.

2. The absorbent product according to claim 1, wherein the first and second panel sections are constituted by a non-elastic material.

3. The absorbent product according to claim 2, wherein the tabs are equal in size.

4. The absorbent product according to claim 3, wherein the first tab and the second tab are rectangular.

5. The absorbent product according to claim 1, wherein the tabs are equal in size.

6. The absorbent product according to claim 1, wherein the first tab and the second tab are rectangular.

7. The absorbent product of claim 1, wherein the absorbent product is a pull-up diaper.

8. The absorbent product according to claim 1, wherein each fastener includes a mechanical fastener comprising male members.

9. The absorbent product according to claim 1, wherein a material web from which the side panels are made has a structure comprising female members.

10. The absorbent product according to claim 1, wherein the side portions and the tabs are made from the same material.

* * * * *